(12) United States Patent
Kleyman et al.

(10) Patent No.: US 8,920,314 B2
(45) Date of Patent: Dec. 30, 2014

(54) UNIVERSAL HEIGHT FOAM PORT

(75) Inventors: Gennady Kleyman, Brooklyn, NY (US); Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 351 days.

(21) Appl. No.: 12/895,892

(22) Filed: Oct. 1, 2010

(65) Prior Publication Data
US 2011/0082341 A1   Apr. 7, 2011

Related U.S. Application Data

(60) Provisional application No. 61/249,421, filed on Oct. 7, 2010, provisional application No. 61/323,013, filed on Apr. 12, 2010.

(51) Int. Cl.
*A61B 1/32* (2006.01)
*A61B 17/34* (2006.01)

(52) U.S. Cl.
CPC ..... *A61B 17/3423* (2013.01); *A61B 2017/3443* (2013.01); *A61B 2017/3435* (2013.01); *A61B 2017/3466* (2013.01); *A61B 2017/3445* (2013.01); *A61B 17/3462* (2013.01); *A61B 17/3421* (2013.01); *A61B 2017/3429* (2013.01)
USPC ...................................... 600/206

(58) Field of Classification Search
USPC ......... 600/201–209, 192, 194, 210, 215, 221, 600/227, 229, 233; 604/164.01–164.09, 604/164.1–164.13, 165.01–165.04, 166.01, 604/167.01–167.06, 288.01–288.04; 606/213, 201, 215, 108, 185
See application file for complete search history.

(56) References Cited

U.S. PATENT DOCUMENTS

| | | | |
|---|---|---|---|
| 5,375,588 A | 12/1994 | Yoon | |
| 5,524,644 A | 6/1996 | Crook | |
| 5,649,550 A | 7/1997 | Crook | |
| 5,830,191 A | 11/1998 | Hildwein et al. | |
| 5,842,971 A | 12/1998 | Yoon | |
| 5,906,577 A * | 5/1999 | Beane et al. | 600/207 |
| 5,951,588 A | 9/1999 | Moenning | |

(Continued)

FOREIGN PATENT DOCUMENTS

| | | |
|---|---|---|
| EP | 0950376 | 10/1999 |
| EP | 1 774 918 A1 | 4/2007 |

(Continued)

OTHER PUBLICATIONS

European Search Report for EP 10251751 application, date of completion, Apr. 28, 2011.

(Continued)

*Primary Examiner* — Nicholas Woodall

(57) ABSTRACT

A surgical apparatus for positioning within a tissue tract accessing an underlying body cavity is adapted to tissues having different thicknesses. The surgical apparatus is configured to have different lengths. In one embodiment, the surgical includes a seal anchor member having two ends, and one of which is adapted to fold resulting in a plurality of folded states. Each folded state corresponds to a different length of the seal anchor member. The seal anchor member includes a slot to facilitate transition within the plurality of folded states. The seal anchor member further includes an aperture and a pin configured to further facilitate transition within the plurality of folded states.

15 Claims, 15 Drawing Sheets

(56) References Cited

U.S. PATENT DOCUMENTS

| | | | |
|---|---|---|---|
| 6,018,094 A | 1/2000 | Fox | |
| 6,254,534 B1 | 7/2001 | Butler et al. | |
| 6,382,211 B1 | 5/2002 | Crook | |
| 6,450,983 B1 | 9/2002 | Rambo | |
| 6,454,783 B1 | 9/2002 | Piskun | |
| 6,582,364 B2 | 6/2003 | Butler et al. | |
| 6,613,952 B2 | 9/2003 | Rambo | |
| 6,723,044 B2 | 4/2004 | Pulford et al. | |
| 6,814,078 B2 | 11/2004 | Crook | |
| 6,846,287 B2 | 1/2005 | Bonadino et al. | |
| 6,958,037 B2 | 10/2005 | Ewers et al. | |
| 7,033,319 B2 | 4/2006 | Pulford et al. | |
| 7,052,454 B2 * | 5/2006 | Taylor | 600/114 |
| 7,081,089 B2 | 7/2006 | Bonadio et al. | |
| 7,238,154 B2 | 7/2007 | Ewers et al. | |
| 7,300,399 B2 | 11/2007 | Bonadio et al. | |
| 7,377,898 B2 | 5/2008 | Ewers et al. | |
| 7,473,221 B2 | 1/2009 | Ewers et al. | |
| 7,650,887 B2 | 1/2010 | Nguyen et al. | |
| 7,704,207 B2 | 4/2010 | Albrecht et al. | |
| 7,727,146 B2 | 6/2010 | Albrecht et al. | |
| 7,798,898 B2 | 9/2010 | Luciano, Jr. et al. | |
| 7,909,760 B2 | 3/2011 | Albrecht et al. | |
| 2004/0049099 A1 * | 3/2004 | Ewers et al. | 600/206 |
| 2005/0096695 A1 | 5/2005 | Olich | |
| 2005/0192483 A1 | 9/2005 | Bonadio et al. | |
| 2005/0241647 A1 | 11/2005 | Nguyen et al. | |
| 2005/0288558 A1 | 12/2005 | Ewers et al. | |
| 2006/0241651 A1 * | 10/2006 | Wilk | 606/108 |
| 2006/0247499 A1 | 11/2006 | Butler et al. | |
| 2007/0149859 A1 | 6/2007 | Albrecht et al. | |
| 2008/0255519 A1 | 10/2008 | Piskun et al. | |
| 2008/0319261 A1 | 12/2008 | Lucini | |
| 2009/0036738 A1 | 2/2009 | Cuschieri | |
| 2009/0093752 A1 | 4/2009 | Richard et al. | |
| 2009/0093850 A1 | 4/2009 | Richard | |
| 2009/0326332 A1 | 12/2009 | Carter | |
| 2010/0100043 A1 | 4/2010 | Racenet | |
| 2010/0234688 A1 * | 9/2010 | Carter | 600/208 |
| 2010/0240960 A1 | 9/2010 | Richard | |
| 2011/0034778 A1 | 2/2011 | Kleyman | |
| 2011/0082341 A1 | 4/2011 | Kleyman et al. | |
| 2011/0125186 A1 | 5/2011 | Fowler et al. | |
| 2011/0251463 A1 | 10/2011 | Kleyman | |
| 2011/0251464 A1 | 10/2011 | Kleyman | |
| 2011/0251465 A1 | 10/2011 | Kleyman | |
| 2011/0251466 A1 | 10/2011 | Kleyman et al. | |

FOREIGN PATENT DOCUMENTS

| | | |
|---|---|---|
| EP | 2044889 A1 | 4/2009 |
| WO | WO 97/33520 | 9/1997 |
| WO | WO 99/16368 | 4/1999 |
| WO | WO 01/49363 A1 | 7/2001 |
| WO | WO 03/034908 A2 | 5/2003 |
| WO | WO 2004/054456 A1 | 7/2004 |
| WO | 2004/075741 A2 | 9/2004 |
| WO | WO 2004/075741 | 9/2004 |
| WO | WO 2008/042005 | 4/2008 |
| WO | WO 2008/093313 A1 | 8/2008 |
| WO | WO 2008/121294 A1 | 10/2008 |

OTHER PUBLICATIONS

U.S. Appl. No. 13/091,246, filed Apr. 21, 2011, Paul D. Richard.
U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13/217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okoniewski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report for corresponding EP 10251751 date of mailing is Jan. 20, 2011 (4 pages).

* cited by examiner

UNIVERSAL HEIGHT FOAM PORT

CROSS-REFERENCE TO RELATED APPLICATIONS

The present application claims priority to, and the benefit of, U.S. Provisional Application Ser. No. 61/249,421 filed Oct. 7, 2009, and U.S. Provisional Application Ser. No. 61/323,013 filed Apr. 12, 2010. The entire contents of these prior applications are hereby incorporated by reference.

BACKGROUND

1. Technical Field

The present disclosure relates generally to surgical apparatuses for use in minimally invasive surgical procedures, such as endoscopic and/or laparoscopic procedures, and more particularly, relates to a surgical apparatus that allows multiple surgical instruments to be inserted through a single incision.

2. Description of Related Art

Today, many surgical procedures are performed through small incisions in the skin, as compared to large incisions that are typically required in traditional procedures, in an effort to reduce trauma to the patient and reduce the patient's recovery time. Generally, such procedures are referred to as "endoscopic", unless performed on the patient's abdomen, in which case the procedure is referred to as "laparoscopic." Throughout the present disclosure, the term "minimally invasive" should be understood to encompass both endoscopic and laparoscopic procedures.

During a typical minimally invasive procedure, surgical objects, such as endoscopes, graspers, staplers and forceps, are inserted into the patient's body through the incision in tissue. In general, prior to the introduction of the surgical object into the patient's body, insufflation gas is supplied to the target surgical site to enlarge its surrounding area and create a larger, more accessible work area. Accordingly, a substantially fluid-tight seal is desirable to inhibit the escape of the insufflation gas and avoid the deflation or collapse of the enlarged surgical site.

Different patients have different tissue thicknesses. Generally, access devices of different lengths are supplied in order to meet patients' various demands based on their various tissue thicknesses. Such prior access devices have numerous disadvantages both from the standpoint of design as well as from the standpoint of availability of use.

From the design perspective, no one single prior access device is universally suitable for tissues having different thicknesses. In the prior art, each access device is designed in contemplation of a tissue having a particular thickness. Thus, access devices of different lengths have to be designed and supplied in order to accommodate patients with different needs based on their tissue thicknesses.

In the use of prior access devices, patient's tissue thickness needs to be assessed before performing a minimally invasive procedure. After assessing the tissue thickness and before performing the procedure, an access device having a length suitable for the patient's tissue thickness is selected. An error made in the assessment may lead to consequences adversely impacting the procedure. For instance, if the assessment underestimates the patent's tissue thickness, then an access device having a length less than the patient's tissue thickness is selected. On the other hand, if the assessment overestimates the patient's thickness, an access device of a length greater than the patient's tissue thickness is selected. In both scenarios, the selected access devices cannot be stabilized within the patient's incision, thus are inadequate for the procedure.

Therefore, to avoid the need of designing and supplying access devices of different lengths, to preclude the need of assessing tissue thickness, and to avoid unnecessary problems caused by erroneous assessments, it is desirable to have a single access device that can be configured to different lengths, such that the single access device can be suitable for tissues having different thicknesses.

SUMMARY

Disclosed herein is a surgical apparatus for positioning within a tissue tract accessing an underlying body cavity. The surgical apparatus comprises a seal anchor member. The seal anchor member has a longitudinal axis, a length, a first end and a second end. Please note that all embodiments of the seal anchor member discussed below may define a substantial length along the longitudinal axis for accommodating thick tissues in bariatric related procedures. The first end of the seal anchor member is configured to fold along the longitudinal axis, resulting in a plurality of states. Each state corresponds to a different length of the seal anchor member.

In one embodiment, the plurality of states comprises a plurality of folded states. In each folded state, the first end has an outer surface and an inner surface. Each folded state is maintained by connecting the outer surface and the inner surface of the first end together. The plurality of folded states includes a maximum folded state and a minimum folded state. In the maximum folded state, the length of the seal anchor member is minimized. In contrast, in the minimum folded state, the length of the seal anchor member is maximized.

In another embodiment, the plurality of states further comprises an unfolded state in which the first end of the seal anchor member is not folded. Similar to the embodiment described above, the length of the seal anchor is minimized in the maximum folded state. Unlike the embodiment described above, the length of the seal anchor member is maximized in the unfolded state.

In a certain embodiment, the first end of the seal anchor member defines a slot to facilitate transition among the plurality of folded states. Further, the first end defines an aperture through which a pin is used to further facilitate transition between the maximum and minimum folded states. The pin further connects the outer surface and the inner surface together to maintain a folded state.

In an alternate embodiment, a surgeon manually adjusts the length of the outer surface and the length of the inner surface of the first end in order to select a desired folded state. After making the selection, the surgeon uses a suture to hold the inner surface and the outer surface of the first end together to secure and maintain the selected folded state.

In a certain embodiment, the first end defines a substantially large radial diameter thereby increasing the range of motion of the surgical instruments inserted therein. The second end defines a substantially small radial diameter thereby providing an easy insertion and removal of the seal anchor member through tissues.

In an alternate embodiment, the seal anchor member defines a coring configuration such that there is a large free open space within the seal anchor member that increases the range of motion of the surgical instruments inserted therethrough.

In a preferred embodiment, the seal anchor member defines at least four longitudinal ports extending therethrough. Each longitudinal port is configured to accommodate a surgical instrument.

In another embodiment, the seal anchor member defines at least one slit between adjacent longitudinal ports. The at least one slit extends longitudinally between the first and second ends and terminates before reaching the second end. The at least one slit defines a length less than the distance from the first end to the second end. The at least one slit reduces interferences that otherwise may occur between adjacent longitudinal ports or between instruments inserted in adjacent longitudinal ports.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
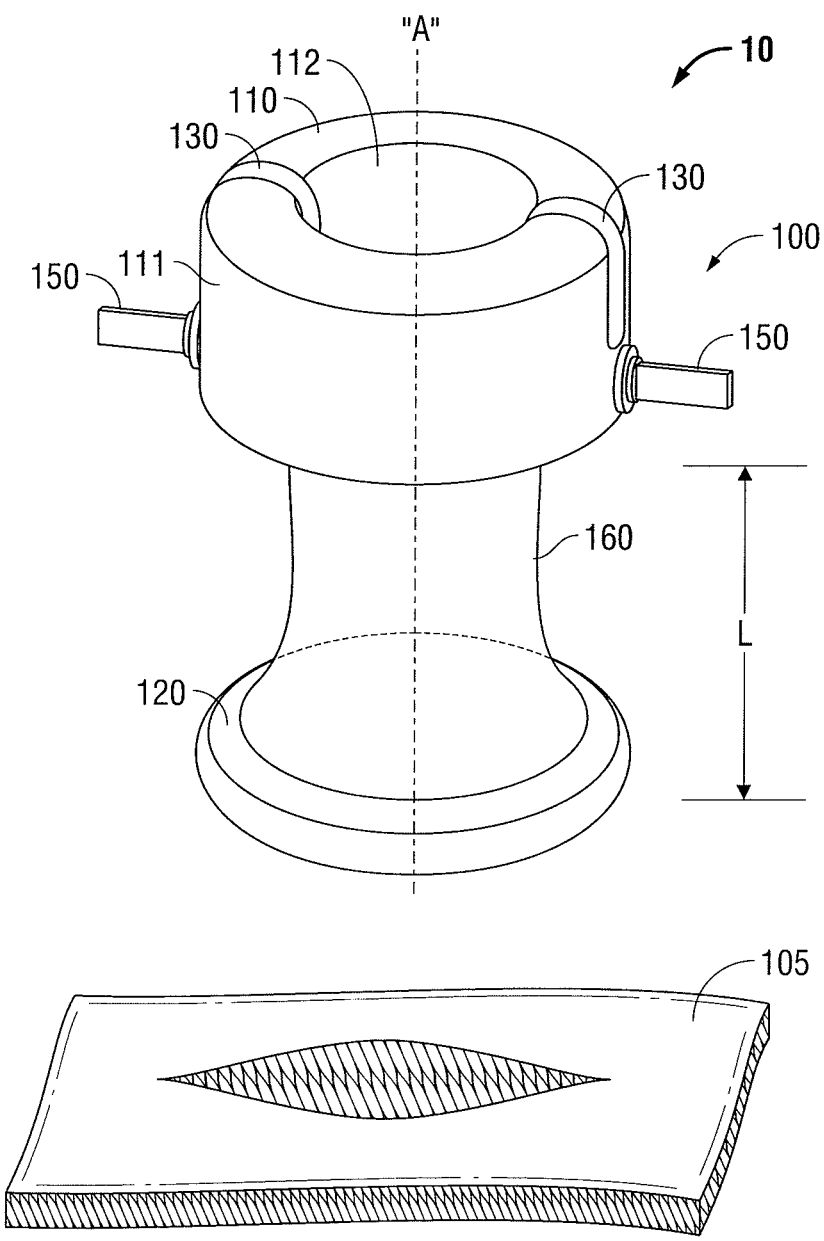
FIG. 1 is a front perspective view of a surgical apparatus in accordance with the principles of the present disclosure illustrating a seal anchor member positioned relative to the tissue.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein employs a device that facilitates multiple instrument access through a single incision. This is a minimally invasive surgical procedure, which permits a user to operate through a single entry point, typically the patient's navel. Additionally, the presently disclosed device may be used in a procedure where a naturally occurring orifice (e.g. vagina or anus) is the point of entry to the surgical site. The disclosed procedure involves insufflating the body cavity and positioning a portal member within, e.g., the navel of the patient. Instruments including an endoscope and additional instruments such as graspers, staplers, forceps or the like may be introduced within a portal member to carry out the surgical procedure. An example of such a surgical portal is disclosed in commonly assigned U.S. patent application Ser. No. 12/244,024, Pub. No. US 2009/0093752 A1, filed Oct. 2, 2008, the entire contents of which are hereby incorporated by reference herein.

The surgical apparatus described herein below may be used in minimally invasive bariatric surgeries or any other minimally invasive surgeries. In general, obese patients have significantly thick tissues compared to patients of normal weight. During bariatric related treatment procedures, an incision is initially created off the midline for providing an access to the patient's body cavity. Access devices taught by the prior art are oftentimes not tall enough to be placed across the entire abdominal walls of obese patients. Thus, the prior access device cannot be securely placed within incisions, thereby adversely influencing the operation of bariatric procedures. The surgical apparatus of the present invention solves this problem by comprising a seal anchor member defining a substantially large length to accommodate unusually thick tissues in bariatric related treatment procedures. In particular, the seal anchor member defines an intermediate portion that is substantially lengthy along the longitudinal axis of the seal anchor member between the trailing and leading ends thereof. The seal anchor member further includes at least one longitudinal port substantially lengthy along the longitudinal axis "A" thereof between the intermediate portion and the leading end or between the trailing end and the leading end for receiving surgical instruments therethrough. With this configuration, the seal anchor member can be securely placed at the incision extending across a very thick abdominal wall for introducing surgical instruments therethrough to manipulate tissues or organs within the body cavity. Accordingly, the seal anchor member is securely fit with respect to the incision, resulting in a stable state facilitating introduction of surgical instruments therethrough for performing bariatric procedures. Please note all embodiments described herein below may be configured to have a substantial length for use in bariatric procedures.

Referring now to the drawings, in which like reference numerals identify identical or substantially similar parts throughout the several views, FIG. 1 illustrates a surgical apparatus 10 comprising a seal anchor member 100 in accordance with the principles of the present disclosure. Seal anchor member 100 is adapted for insertion within a tissue tract 105, e.g., through the abdominal or peritoneal lining in connection with a laparoscopic surgical procedure. The seal anchor member 100 will be described in greater detail hereinbelow.

With reference to FIG. 1, the seal anchor member 100 defines a longitudinal axis "A" and a length "L". The length "L" relates to the distance of the portion of the seal anchor member 100 that can be inserted through the tissue tract 105. The seal anchor member 100 has respective trailing and leading ends 110, 120 and an intermediate portion 160 disposed between the trailing and leading ends 110, 120. The seal anchor member 100 may be made from a semi-resilient, disposable, compressible, and flexible type material, for example, but not limited to, a suitable foam, gel material, or soft rubber having sufficient compliance to form a seal about one or more surgical objects, and also establish a sealing relation with the tissue tract 105 and with the surgical object. In one embodiment, the foam includes a polyisoprene material. As shown in FIG. 1, the seal anchor member 100 may define a substantially hourglass shape. However, it is contemplated that the seal anchor member 100 may define other configurations both prior and subsequent to insertion within the tissue tract 105.

Figure 2:
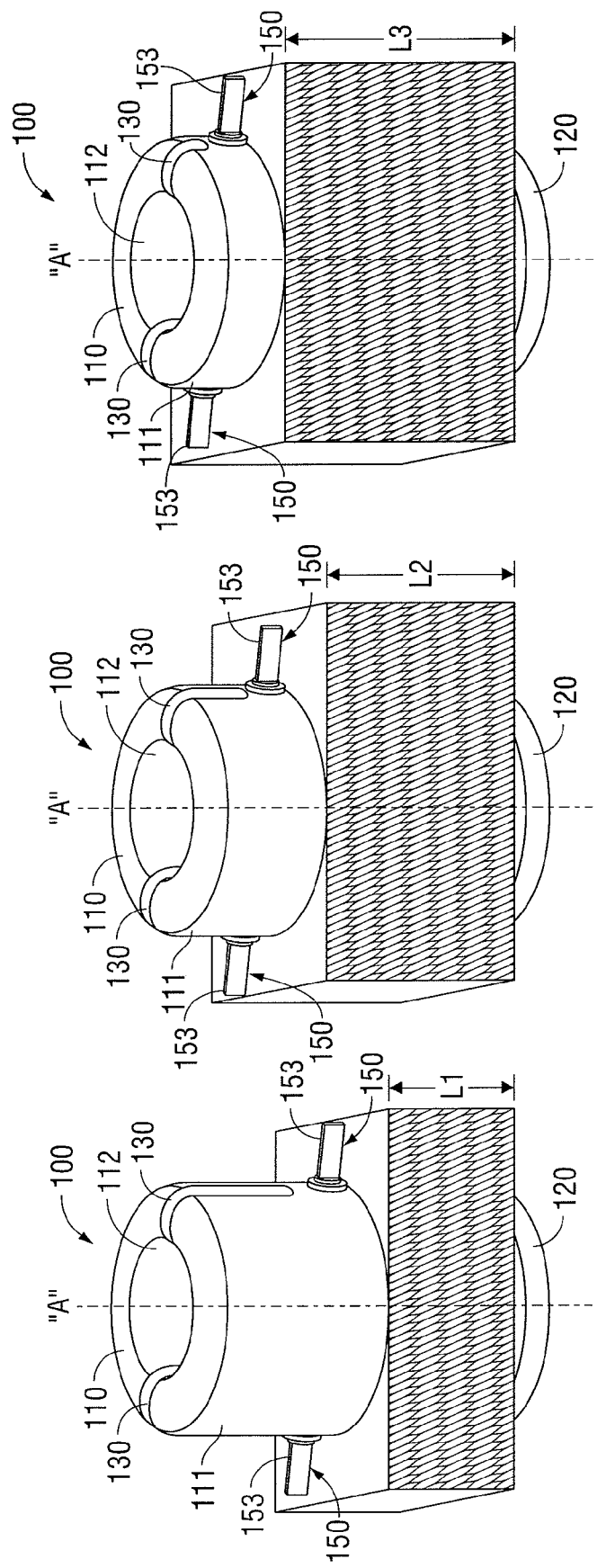
FIG. 2a is a front perspective view of the seal anchor member of FIG. 1 in the maximum folded state.
FIG. 2b is a front perspective view of the seal anchor member of FIG. 1 in an intermediate folded state selected between the maximum and minimum folded states.
FIG. 2c is a front perspective view of the seal anchor member of FIG. 1 in the minimum folded state.

Due to the flexible and semi-resilient characteristics of the seal anchor member 100, the length "L" of seal anchor member 100 can be adjusted to be suitable for tissues having different thicknesses. In one embodiment, as illustrated in FIG. 1, to adjust the length "L" of the seal anchor member 100, the trailing end 110 is configured to fold at any position along the longitudinal axis "A" thus resulting in various lengths "L". As best illustrated in FIGS. 2a-2c, the trailing end 110 is configured to define a plurality of folded states. Each of the three folded states in FIGS. 2a-2c corresponds to a different length of the seal anchor member 100, namely, "L1", "L2" and "L3", respectively. The trailing end 110 in each folded state defines an outer surface 111 and an inner surface 112. The outer surface 111 is formed by the portion of the trailing end 110 that is folded along the longitudinal axis "A", whereas the inner surface 112 is formed by the portion of the trailing end 110 that is not yet folded. As the trailing end 110 transits among different folded states, portions of the outer surface 111 may gradually merge into the inner surface 112, and vice versa.

The plurality of the folded states range between a maximum folded state as shown in FIG. 2a and a minimum folded state as shown in FIG. 2c. The maximum folded state describes a state in which a maximum portion of the trailing end 110 is folded downwardly, thus resulting in a minimum length "L" of the seal anchor member 100. In contrast, the minimum folded state occurs when a minimum portion of the trailing end 110 is folded, resulting in a maximum length "L" of the seal anchor member 100. As a result, the seal anchor member 100 can be adapted to tissue having different thicknesses by simply adjusting its length "L".

Figure 3:
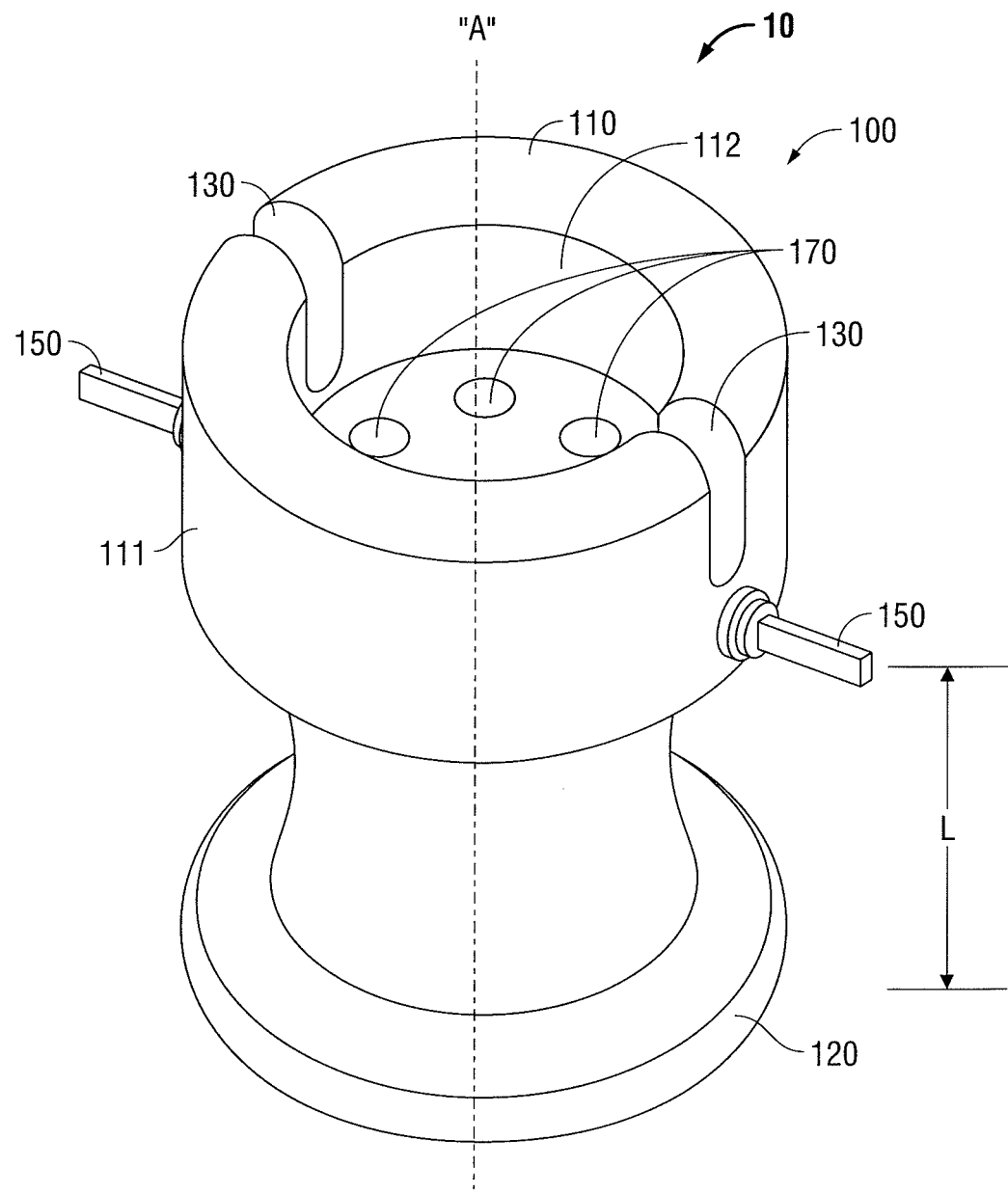
FIG. 3 is a front perspective view of the seal anchor member of FIG. 1 illustrating the trailing end of the seal anchor member.
Figure 4:
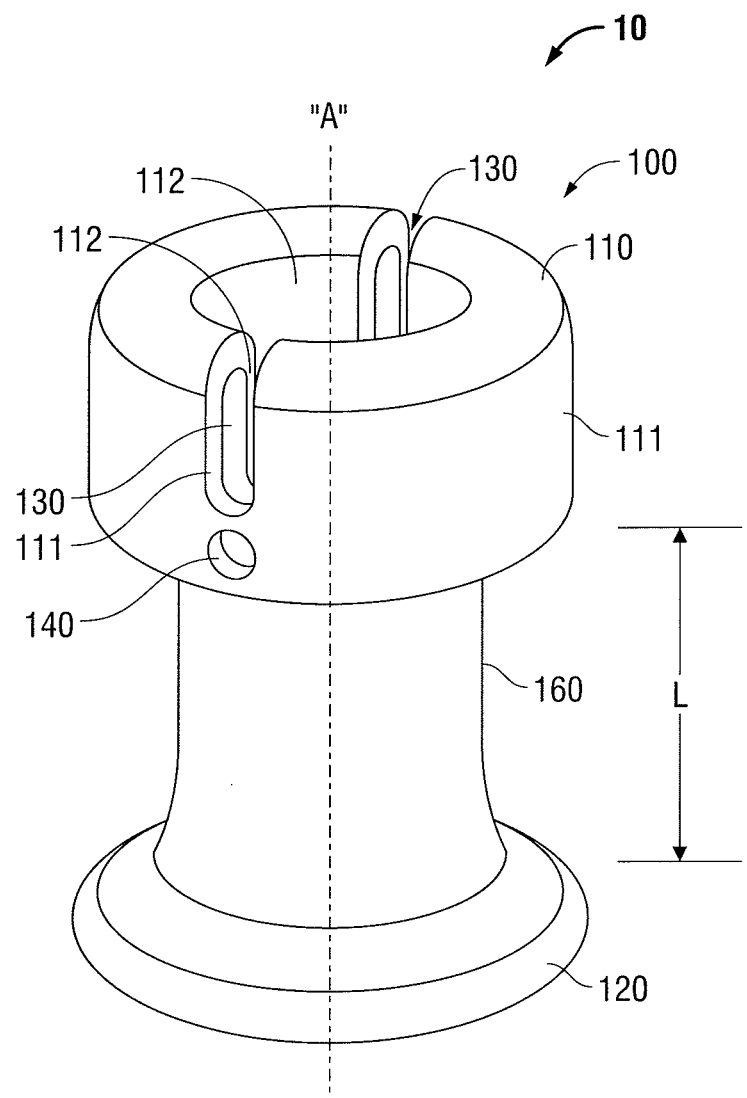
FIG. 4 is a perspective view of the seal anchor member of FIG. 1 illustrating the slot and the aperture of the trailing end.
Figure 5:
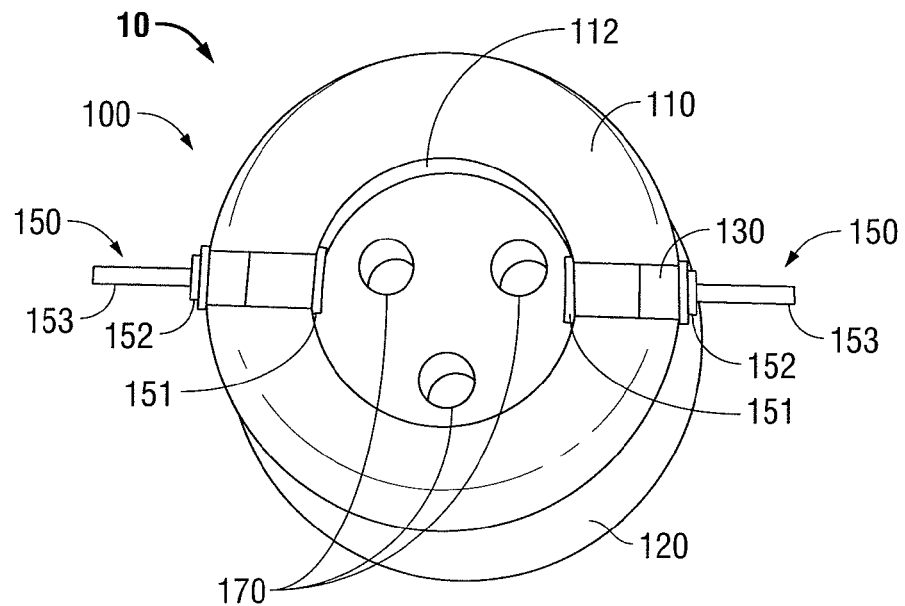
FIG. 5 is a top perspective view of the seal anchor member of FIG. 1 illustrating a plurality of ports extending longitudinally therethrough.

To facilitate transition between the maximum and minimum folded states, the trailing end 110 defines two slots 130, as illustrated in FIG. 3. Each slot 130 spans across the outer surface 111 and the inner surface 112 of the trialing end 110. The two slots 130 are diametrically opposed on the trailing end 110. As illustrated in FIG. 4, each slot 130 corresponds to an aperture 140. Each aperture 140 is positioned directly beneath its corresponding slot 130 on the outer surface 111 of the trailing end 110. With reference to FIG. 5, each slot 130 further engages a pin 150 which is positioned across the outer surface 111 and the inner surface 112 of the trailing end 110. Each pin 150 includes a head 151, a body 152, and a handle 153. The body 152 extends across the outer surface 111 via the aperture 140 and the inner surface 112 via the slot 130. The body 152 is attached firmly to the outer surface 111 of the trailing end 110 at the aperture 140. Further, a handle 153 protrudes outwardly beyond the outer surface 111 and is used by a surgeon to adjust the position of the pin 150 to adjust the position of pin 150 along the longitudinal axis "A." Further, a head 151 extends inwardly beyond the inner surface 112 and is placed against the inner surface 112. The head 151 has a diameter greater than that of the body 152.

With continued reference to FIG. 5, the pin 150 is configured to slide along the longitudinal length of the slot 130 by moving the handle 153 up and down along the longitudinal axis "A." Essentially, the slot 130 provides a passageway that guides the pin 150 to slide longitudinally under the control of the handle 153. As the pin 150 slides from one end of the slot 130 to the other end of the slot 130, the trailing end 110 undergoes a transition between the maximum folded state and the minimum folded state. Accordingly, the seal anchor member 100 is adjustable between the minimum length "L" and the maximum length "L". Further details regarding this transition are explained below.

With reference to FIGS. 2a-2c, as the handle 153 is lifted in an upward direction along the longitudinal axis "A", portions of the outer surface 111 gradually merge into the inner surface 112, thereby transitioning the trailing end 110 from a more folded state, as shown in FIG. 2a, to a less folded state, as shown in FIG. 2c, resulting in an increased length "L" of the seal anchor member 100. In contrast, as the handle 153 is pushed in a downward direction along the longitudinal axis "A", portions of the inner surface 112 gradually merge into the outer surface 111, thereby transitioning the trailing end 110 from a less folded state, shown in FIG. 2c, to a more folded state, as shown in FIG. 2a, resulting in a decreased length "L" of the seal anchor member 100. Thus, the surgeon can adjust the length "L" of the seal anchor member 100 by moving the handle 153 along the longitudinal axis "A" until a desired length "L" is reached.

Figure 6:
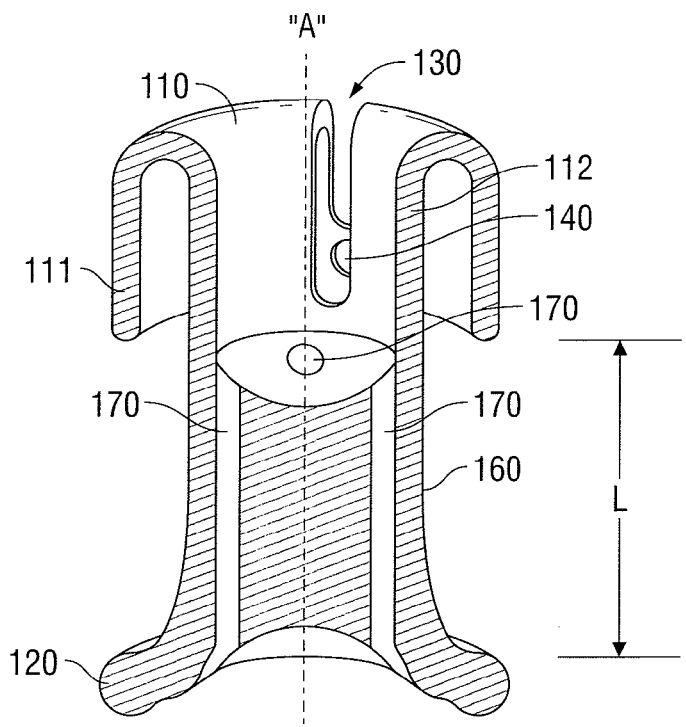
FIG. 6 is a side cross-sectional view of the seal anchor member of FIG. 1 illustrating a port that extends longitudinally through the leading end and the intermediate portion of the seal anchor member.

With reference to FIGS. 5 and 6, the trailing end 110 exhibits an elongated, tubular structure defining a hollow center region, as shown in FIG. 6. The seal anchor member 100 further includes at least one longitudinal port 170 extending along the longitudinal axis "A" of the seal anchor member 100 between the leading end 120 and the intermediate portion 160. The ports 170 are configured symmetrically with respect to the longitudinal axis "A". The ports 170 are spaced equidistant from the longitudinal axis "A". Each port 170 may be spaced equidistant from its neighboring ports. Each port 170 is dimensioned to receive a surgical object, e.g. a surgical instrument (not shown) therethrough. Upon introduction of a surgical object (not shown) through a port 170, the port 170 establishes and maintains a substantial sealed relation about the surgical object.

Pins, apertures and slots together constitute one exemplary means of selecting, securing and maintaining a desired folded state. Other fastening means are also envisioned for securing and maintaining a selected folded state. For instance, it is envisioned that the outer surface 111 and the inner surface 112 of the trailing end 110 may be clipped, snapped or hooked in place to secure and maintain the selected folded state. It is also envisioned that that the material of the seal anchor member may also facilitate securing and maintaining the selected folded state in the absence of any other fastening means.

Figure 7:
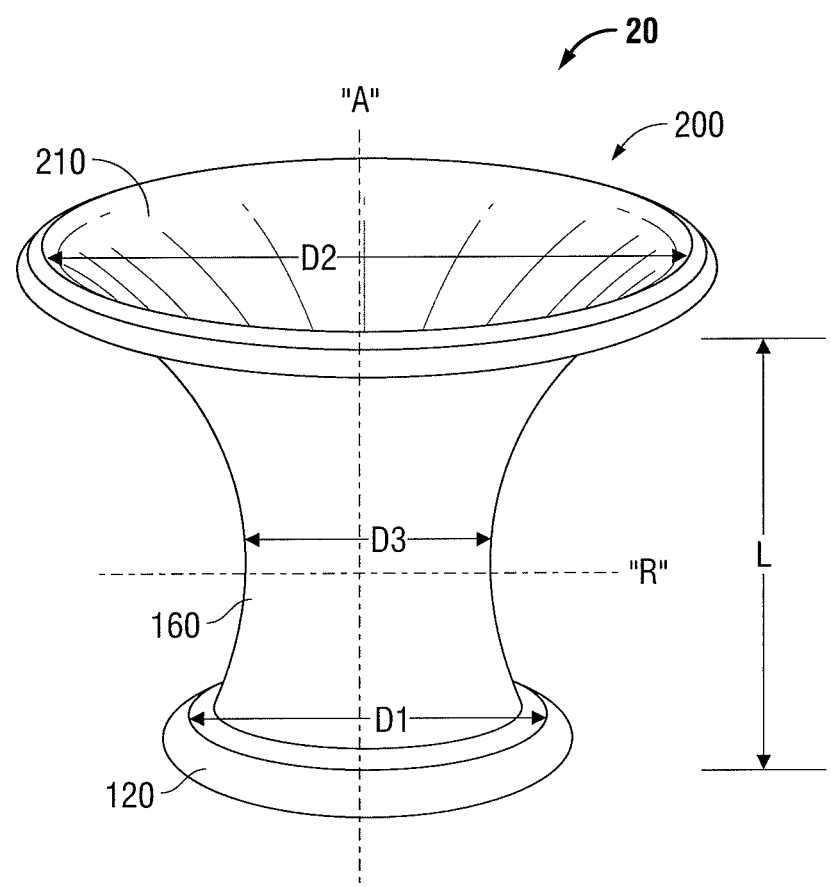
FIG. 7 is a front prospective view of an alternate embodiment of the seal anchor member in an unfolded state.
Figure 8:
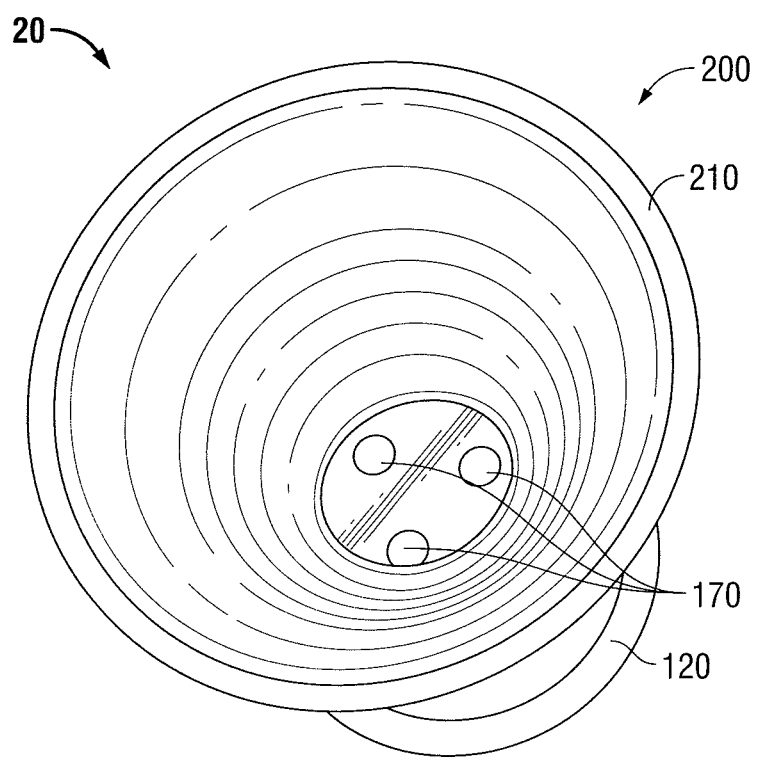
FIG. 8 is a top prospective view of the seal anchor member of FIG. 7.

Turning now to FIGS. 7-13, a surgical apparatus 20 including a seal anchor member 200 will now be described. The seal anchor member 200 includes a leading end 120, an intermediate portion 160, and a trailing end 210. A plurality of ports 170 is disposed between the intermediate portion 160 and the leading end 120 as illustrated in FIG. 8. As illustrated in FIG. 7, the trailing end 210 has an unfolded state in which the trailing end 210 is fully unfurled. The seal anchor member 200 reaches its maximum length "L" when the trailing end 210 is in the unfolded state. The leading end 120 defines a radial diameter "D1" measured along a radial axis "R" at its distal-most end. The trailing end 210 defines a radial diameter "D2" at its proximal-most end. The diameter "D2" is substantially larger than the diameter "D1". This particular configuration of the seal anchor member 200 with one end substantially small and the other end substantially large provides many benefits to surgical procedures. For instance, the leading end 120 with its relatively small dimension provides an easy insertion and removal of the seal anchor member 200 through skin tissues, therefore reducing the time required to place and/or displace the seal anchor member 200 through incisions during surgical operations. The leading end 120 of a reduced dimension also reduces friction between the seal anchor member 200 and tissues, ultimately reducing trauma experienced by the patient during insertion and removal of the seal anchor member 200. By contrast, the trailing end 210 defines a diameter that develops gradually larger from "D3" measured at the distal-most end of the trailing end 210, which touches the intermediate portion 160, to "D2" measured at the proximal-most end of the trailing end 210. The trailing end 210 essentially has a frustoconical-like configuration, although may not be a perfect frusto-conical shape. As shown in FIGS. 7-8, the trailing end 210 with its relatively large dimension creates a wide open space above the plurality of ports 170. As a result, the trailing end 210 provides the surgeon a large free space to manipulate portions of the surgical instruments positioned above the ports 170, ultimately resulting in a significantly increased range of motion of the surgical instruments inserted through the seal anchor member 200 and also facilitating off-axis motions of the surgical instruments. Further, since the proximal-most end of the trailing end 210 is substantially larger than the distal-most end of the trailing end 210, the portion of the trailing end 210 that is close to the proximal-most end can be easily folded, ultimately facilitating transition among the plurality of the folded and unfolded states.

Figure 9:
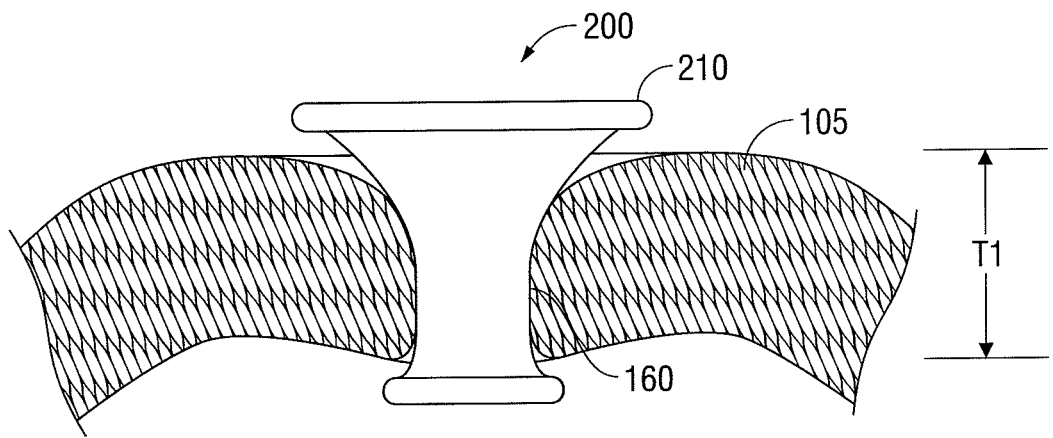
FIG. 9 is a partially cutaway front perspective view of the seal anchor member of FIG. 7 shown in an unfolded state and shown disposed within a tissue tract having a first thickness.
Figure 10:
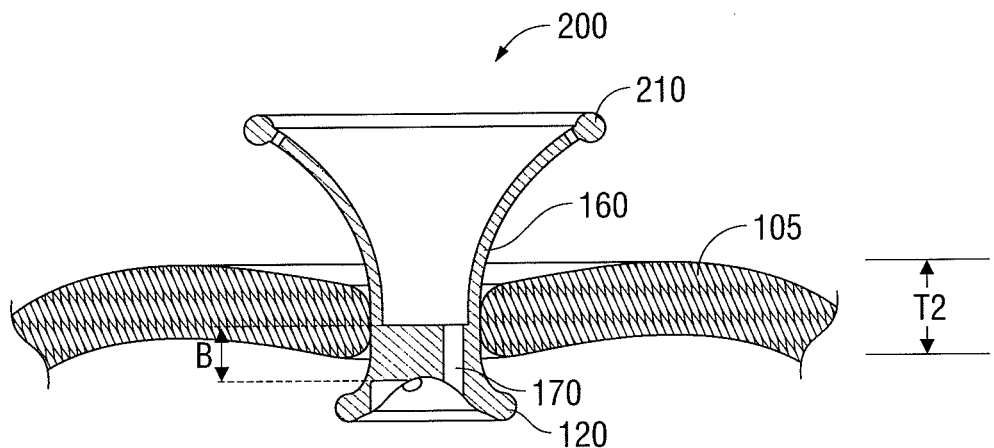
FIG. 10 is a partially cutaway front perspective view of the seal anchor member of FIG. 7 shown in an unfolded state and shown disposed within a tissue tract having a second thickness.
Figure 11:
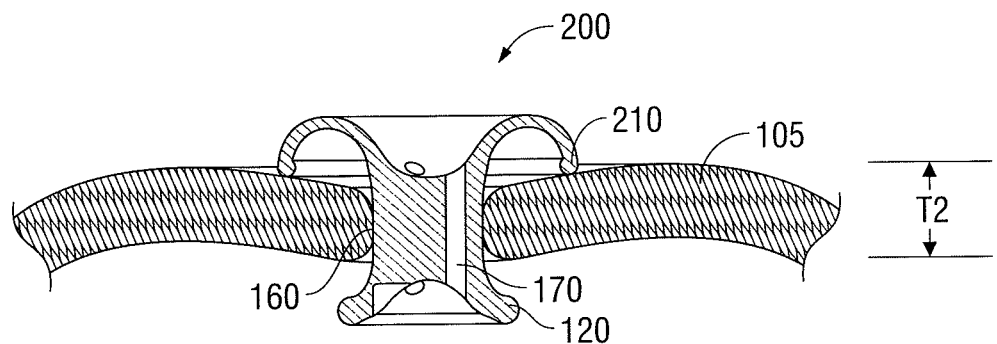
FIG. 11 is a partially cutaway front perspective view of the seal anchor member of FIG. 7 shown in a folded state and shown disposed within the tissue tract of FIG. 10.
Figure 12:
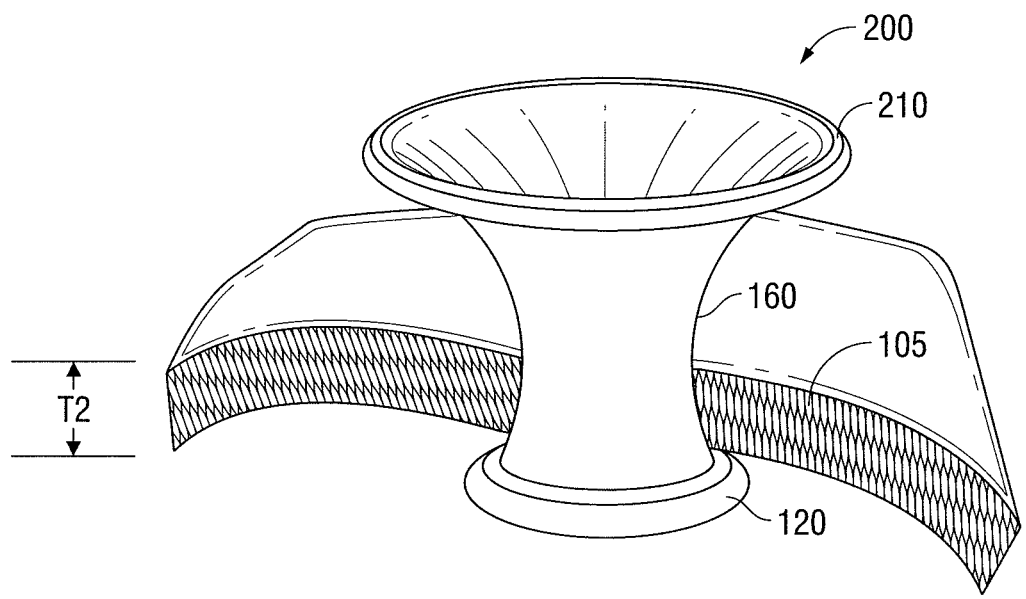
FIG. 12 is a perspective view of the seal anchor member of FIG. 7 shown in an unfolded state and shown disposed within the tissue tract of FIG. 10.
Figure 13:
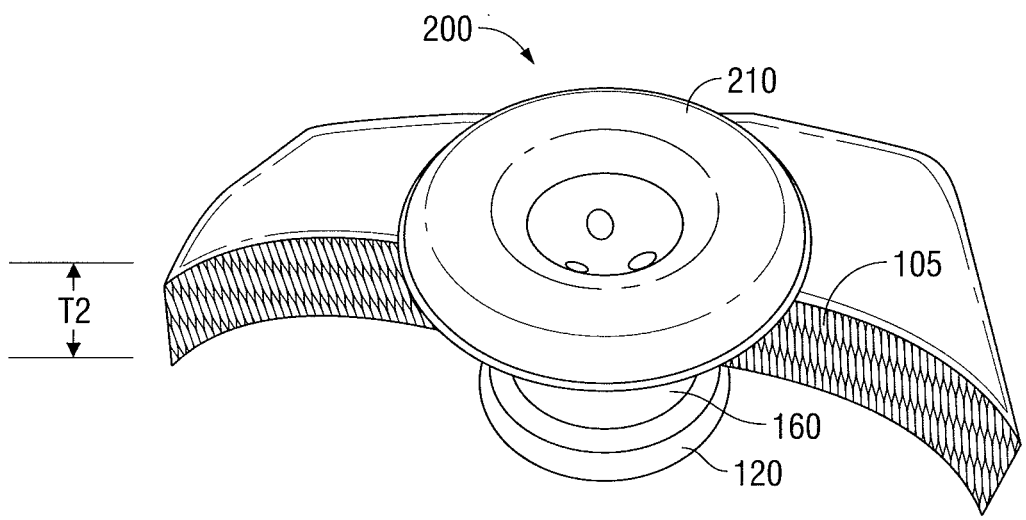
FIG. 13 is a perspective view of the seal anchor member of FIG. 7 illustrated in a folded state and shown disposed within the tissue tract of FIG. 10.

As shown in FIGS. 9-13, the length of the seal anchor member 200 can be adjusted to accommodate tissue tracts 105 having different thicknesses. As seen in FIG. 9, the tissue tract 105 has a thickness "T1" that corresponds to the overall length of the seal anchor member 200 when the seal anchor member 200 is in an unfolded state. In such a situation when the unfolded length of the seal anchor member 200 readily fits in the tissue tract 105, the seal anchor member 200 need not be folded. However, in situations in which the tissue tract 105 has a thickness, e.g., "T2" (FIGS. 10-13), that is less than the unfolded length of the seal anchor member 200, the length of the seal anchor member 200 may be adjusted to approximate thickness T2, as illustrated in FIGS. 11 and 13. As illustrated in FIGS. 11 and 13, the trailing end 210 is folded such that the proximal-most end of the trailing end 210 is moved towards the surface of the tissue tract 105, thereby substantially approximating the thickness "T2".

In another embodiment, the surgical apparatus exhibits a coring configuration as illustrated in FIG. 10, wherein the trailing end 210 and the intermediate portion 160 together define a large free, open space in the center region of the seal anchor member 200 as if a large amount of material has been removed from the seal anchor member 200. The intermediate portion 160 is filled with only a small amount of materials within the region "B" adjacent to the leading end 120, as indicated in FIG. 10. The region "B" defines one or multiple ports 170 for receiving surgical instruments. Therefore, the port 170 in this particular embodiment has a relatively small longitudinal dimension along the longitudinal axis "A". The coring configuration increases the flexibility of the seal anchor member 200 such that the overall shape of the seal anchor member 200 can be easily manipulated. For instance, due to the large empty space within the seal anchor member 200, the seal anchor member 200 can be easily squeezed to facilitate its insertion through incisions. Since the seal anchor member 200 can be easily reduced to a small dimension by squeezing, a large incision opening is no longer necessary for permitting entry of the seal anchor member 200. Therefore, the size of the incision can be considerably reduced as well, ultimately reducing trauma experienced the patient during creation of the incision, as well as reducing the patient's recovery time. Further, the large free space defined above the port 170 increases the maneuverability and the range of motion of the surgical instruments inserted through the seal anchor member 200 and also significantly facilitates off-axis motions of the surgical instruments.

In a preferred embodiment, the seal anchor member defines at least four ports 170, with at least one port for accommodating an instrument connected to an insufflation or evacuation source.

Figure 14:
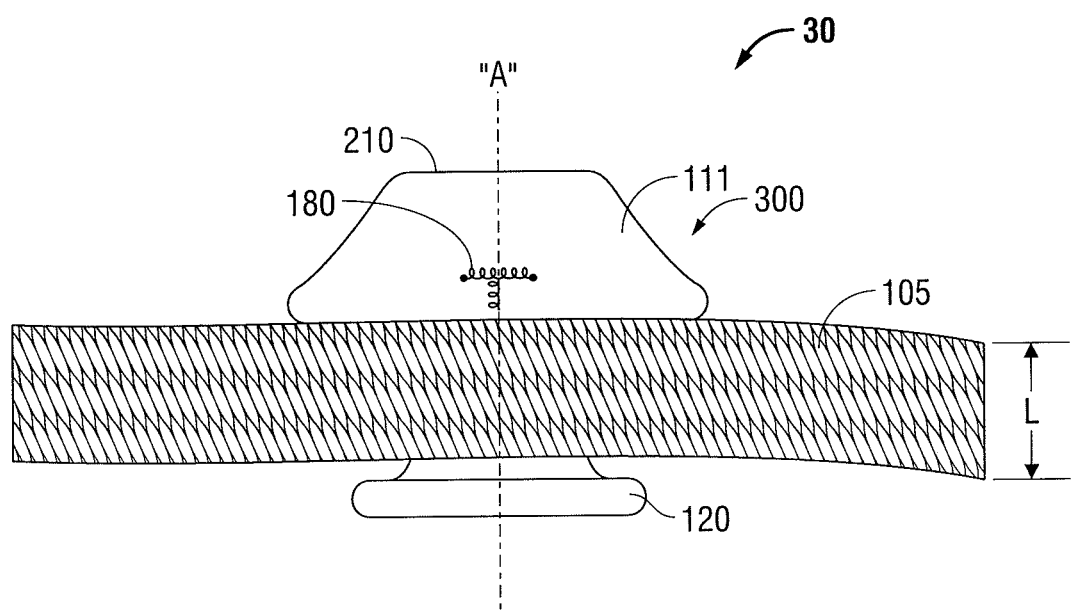
FIG. 14 is a front prospective view yet another embodiment of a seal anchor member shown positioned relative to the tissue.
Figure 15:
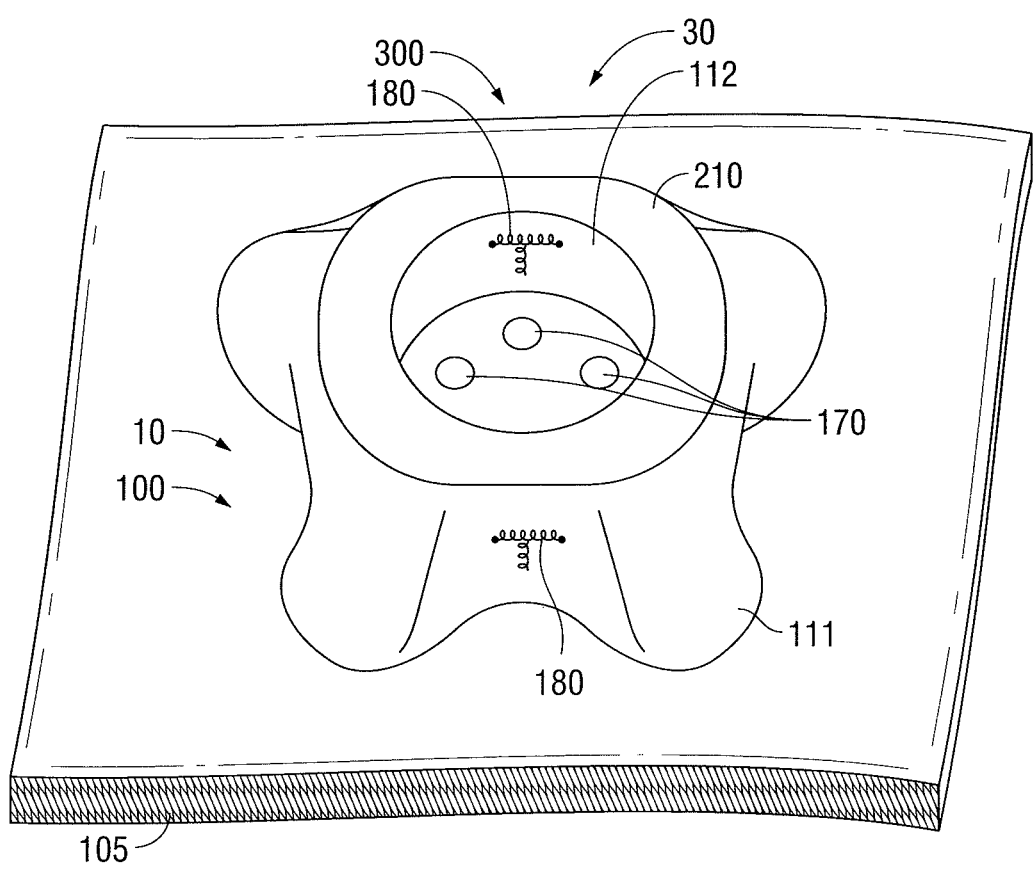
FIG. 15 is a top perspective view of the seal anchor member of FIG. 14.

In a further embodiment, as illustrated in FIGS. 14 and 15, a surgical apparatus 30 includes a seal anchor member 300 including a leading end 120, a trailing end 210, an inner surface 112, an outer surface 111, and a suture 180 adapted to maintain a selected folded state. Upon achieving a desired folded state by folding the trailing end 210, a suture 180 connects the inner surface 112 to the outer surface 111 of the trailing end 110 for purposes of maintaining the selected folded state.

Figure 16:
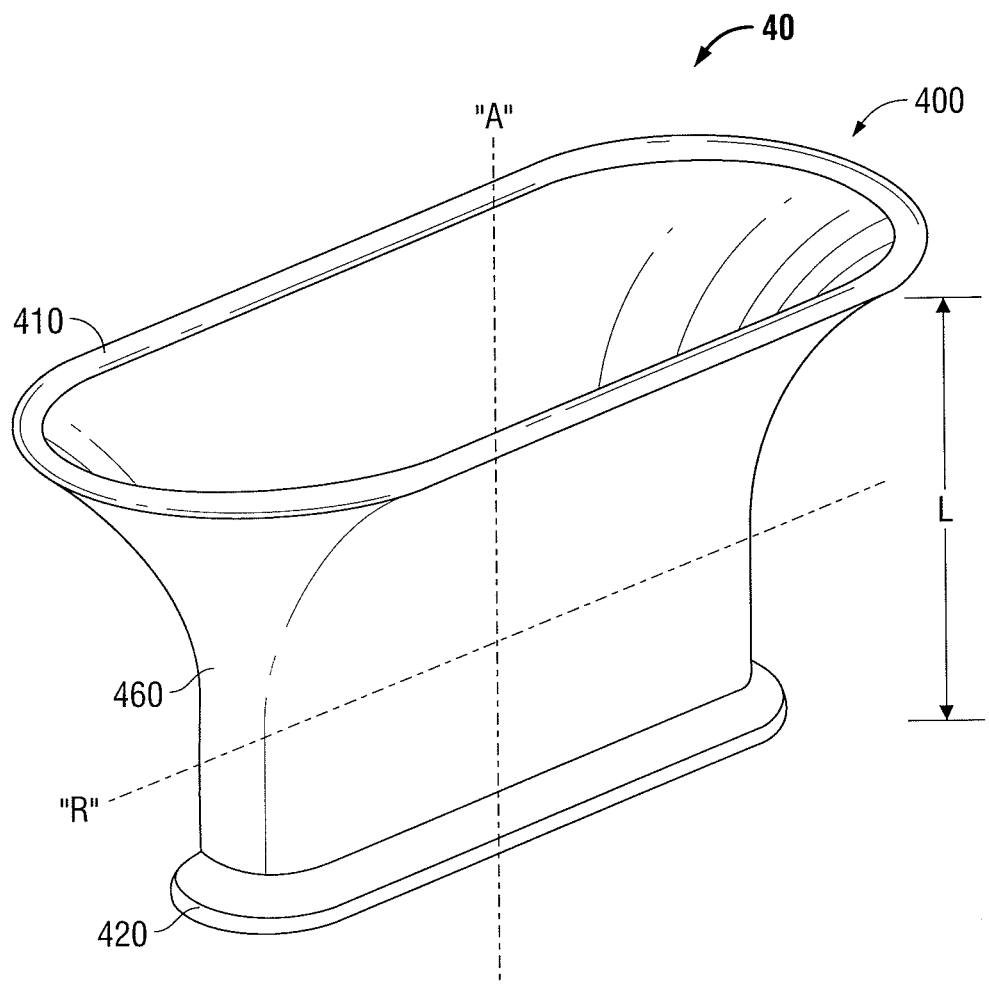
FIG. 16 is a front prospective view of an a still further embodiment of the seal anchor member.
Figure 17:
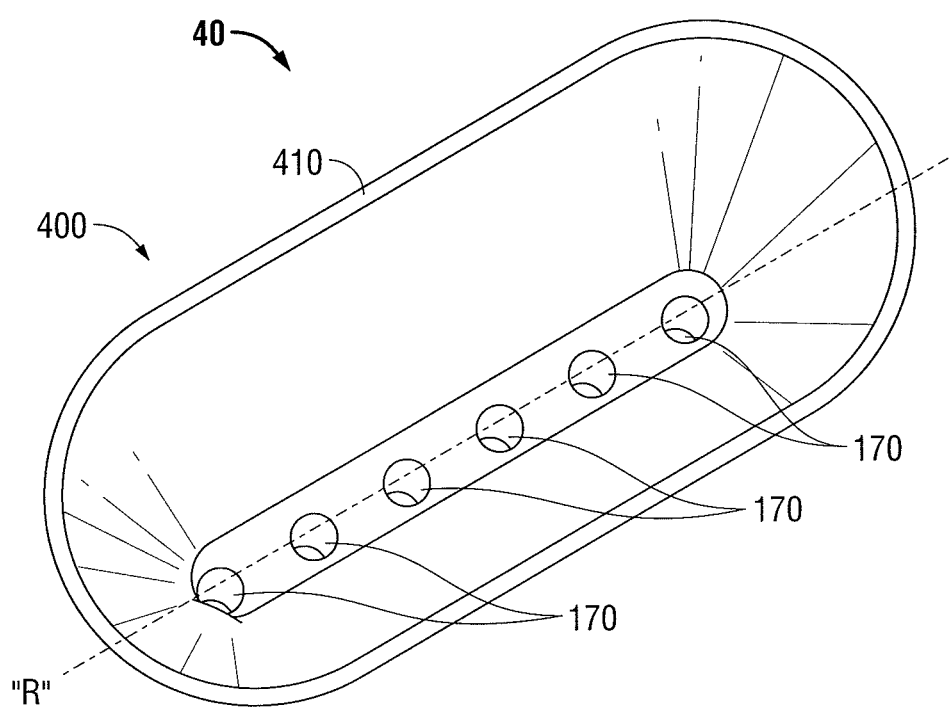
FIG. 17 is a top perspective view of the seal anchor member of FIG. 16.

In a still further embodiment, as illustrated in FIGS. 16 and 17, a surgical apparatus 40 includes a seal anchor member 400. The seal anchor member 400 exhibits an elongated hour-glass configuration and is substantially symmetrical with respect to the longitudinal axis "A." A plurality of ports 170 is disposed within the seal anchor member 400 and arranged in a linear fashion along the radial axis "R." Each port 170 includes a lumen that is substantially parallel to longitudinal axis "A" of the seal anchor member 400. The ports 170 may be equidistantly spaced apart.

Figure 18B:
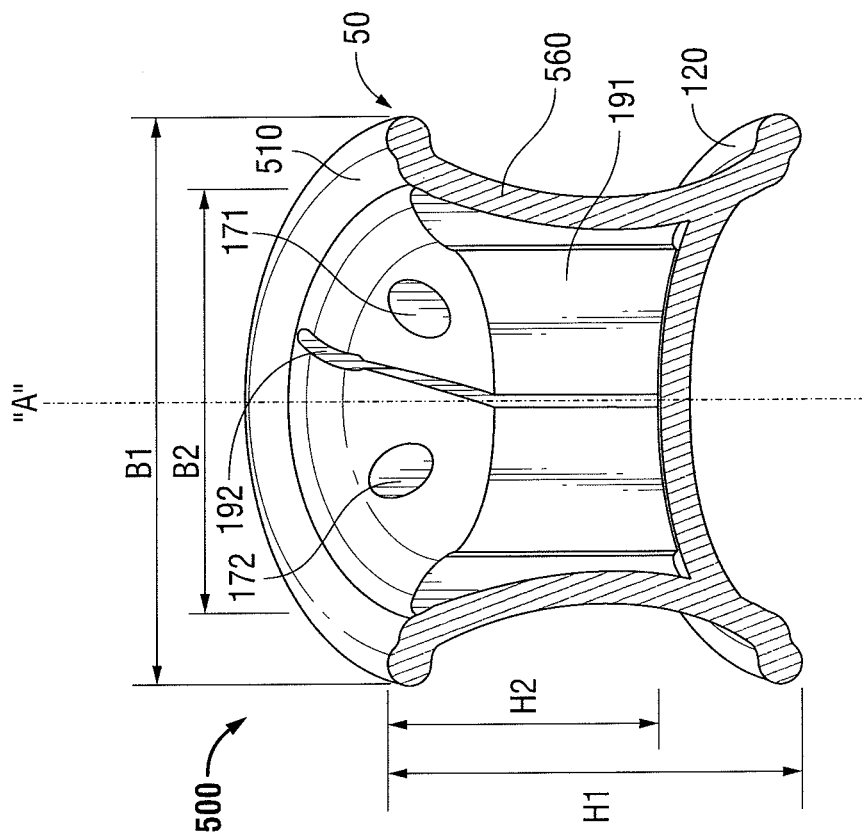
FIG. 18B is a cross-sectional view of the seal anchor member illustrated in FIG. 18A taken along the line 18B-18B.
Figure 18A:
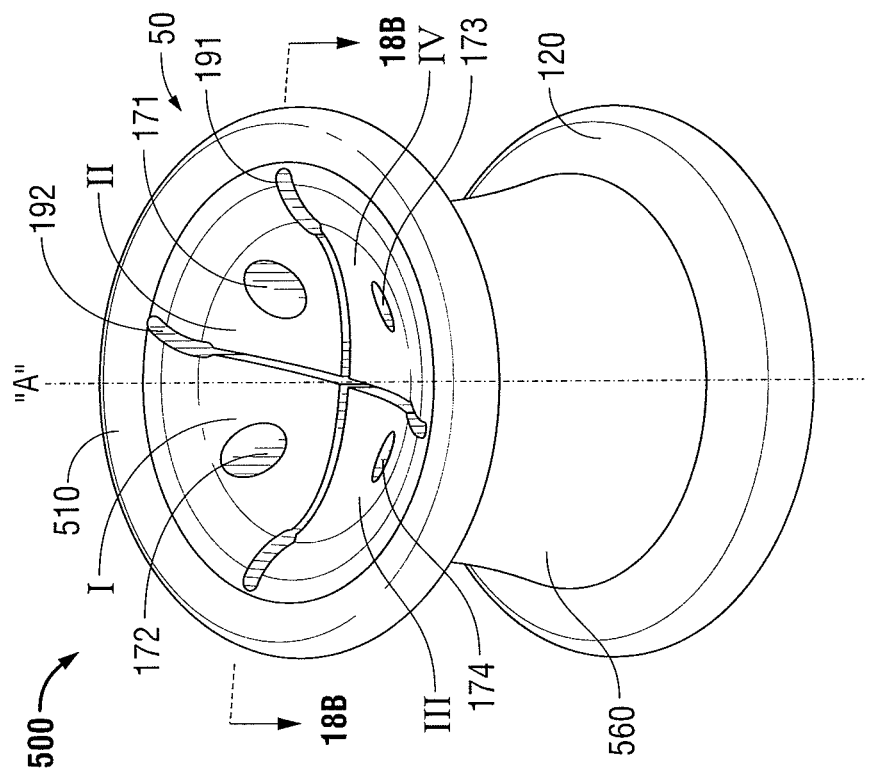
FIG. 18A is a front perspective view of an alternate embodiment of the seal anchor member incorporating slits to separate adjacent ports.

In a certain embodiment, adjacent longitudinal ports are separated by a slit, i.e., a free space, as illustrated in FIGS. 18A-18B. FIGS. 18A-18B illustrate a surgical apparatus 50 comprising a seal anchor member 500 having an hourglass configuration. The seal anchor member 500 defines four longitudinal ports 171, 172, 173 and 174 which are positioned symmetrically about the longitudinal axis "A" and are equidistant from each other. Alternatively, other arrangements of the ports 171-174 are envisioned, such as the distance between adjacent ports may vary. Each longitudinal port in this embodiment has exactly the same characteristics as that of the longitudinal port 170 discussed earlier. Each of the four longitudinal ports 171-174 extends from the trailing end 510 to the leading end 120, providing a passage for surgical instruments to be inserted therein. Each pair of adjacent longitudinal ports is separated by a slit, e.g., 191 and 192. The slits 191 and 192 are formed by removing materials from the member 500, resulting in free space being created between adjacent ports.

In one embodiment, each of the slits 191, 192 is configured to separate two pairs of adjacent ports. For instance, as shown in FIGS. 18A-18B, ports 171 and 172 are separated by slit 192. The same slit 192 also separates ports 174 and 173. Likewise, ports 172 and 174 are separated by slit 191. The same slit 191 also separates sports 171 and 173. Each slit defines a width "B2" that is less than the radial diameter "B1" of the trailing end 510. Each slit also defines a length "H2" that is less than the height "H1" of the member 500 measured from the trailing end 510 to the leading end 120 thereof. Each of the slits 191, 192 does not extend completely through the entire length of the member 500. Rather, each slit extends from the trailing end 510 of the member 500 through the intermediate portion 560, and terminates before reaching the leading end 120.

In one embodiment, the slits are arranged diagonally as seen from the trailing end 510 of the member 500 illustrated in FIG. 18A. The two slits 191 and 192 intersect along the longitudinal axis "A", and separate the seal anchor member 500 into four quadrants "I", "II", "III" and "IV", with one port disposed within each quadrant. For instance, as illustrated in FIG. 18A, the ports 171, 172, 173 and 174 are located in the quadrants "I", "II", "III" and "IV", respectively. All four quadrants are interconnected at the leading end 120. Because each quadrant is spatially set apart from its neighboring quadrant due to the free space defined by the slits, motions that take place within one quadrant is less likely to affect neighboring quadrants. For the above reason, the free space defined by each slit reduces the likelihood of interferences that otherwise may occur between adjacent ports or between instruments placed in adjacent ports. Also, for the same reason, the free space defined by each slit facilitates independent movement of instruments inserted within each individual port. Specifically, the free space defined by each slit facilitates lateral movement or off-axis movement of the instruments positioned within the ports, which, in turn, increases the maneuverability and the range of motion of the instruments inserted within the seal anchor member 500.

Figure 19B:
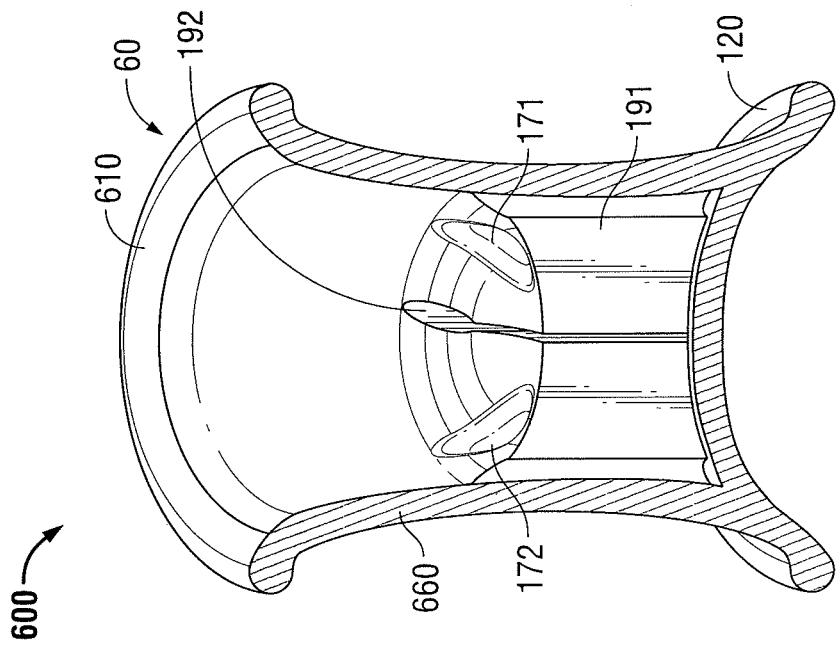
FIG. 19B is a cross-sectional view of the seal anchor member illustrated in FIG. 19A taken along the line 19B-19B.
Figure 19A:
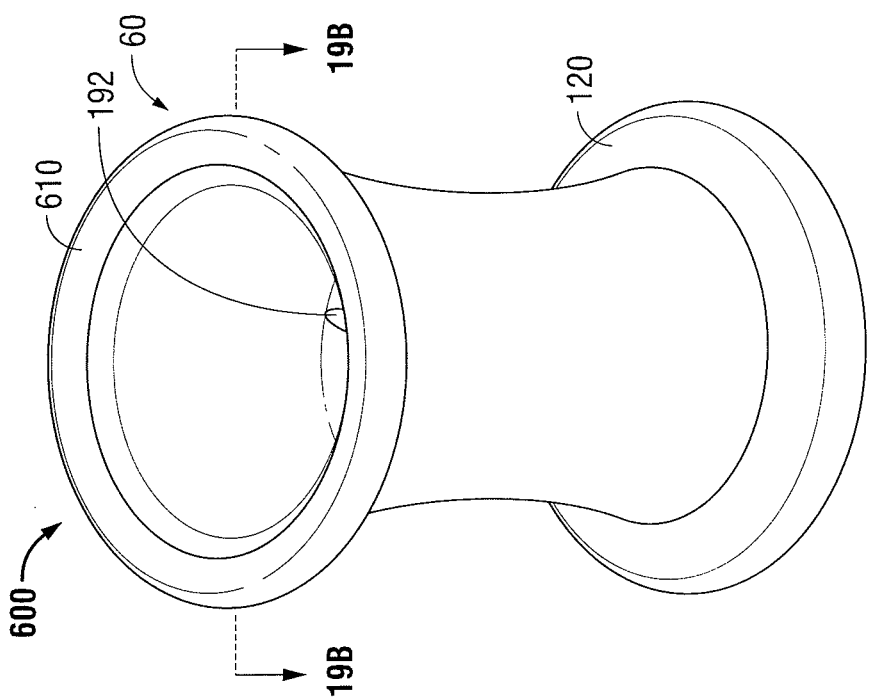
FIG. 19A is a front perspective view of another alternate embodiment of the seal anchor member.

Please note that slits are not a feature limited to the seal anchor member 500 described in FIGS. 18A-18B. It is envisioned that slits may be incorporated into any portal access device, including any one embodiment of the seal anchor member described earlier with respect to FIGS. 1-17. In a certain embodiment illustrated in FIGS. 19A-19B, a seal anchor member 600, which is similar to the seal anchor member 200 illustrated in FIG. 10 in most aspects, has a coring configuration wherein the trailing end 610 and the intermediate portion 660 together define a large free, open space in the center region of the seal anchor member 600 as if a large amount of material has been removed from the seal anchor member 600. The seal anchor member 600 further defines slits 191 and 192 that separate its longitudinal ports, e.g., 171 and 172. The slits 191 and 192 enhances flexibility of the seal anchor member 600, allowing instruments to be easily manipulated and simultaneously minimizing interferences that otherwise may occur between adjacent ports or between instruments inserted in adjacent ports.

Different embodiments of the disclosure may be combined with one another based on the particular needs of the patients to achieve optimal results of the surgical procedures. In one example, in bariatric related procedures, the seal anchor member may define a coring configuration having a substantial length for accommodating thick abdominal walls, and may comprise four longitudinal ports. In another example associated with bariatric related procedures, the seal anchor member may define a coring configuration having a substantial length for accommodating thick abdominal walls, and may further comprise a relatively small leading end, a relatively large trailing end and four longitudinal ports extending therethrough. Any of the presently disclosed embodiments may be used in procedures where access is achieved through a naturally occurring orifice (e.g. vagina or anus).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical apparatus for positioning within a tissue tract accessing an underlying body cavity, which comprises:
    a seal anchor member defining a longitudinal axis and a length, the seal anchor member including a first end and a second end, the first end configured to fold along the longitudinal axis, the first end transitionable to a plurality of states, each state corresponding to a different length of the seal anchor member along the longitudinal axis, the first end including an inner portion and a folded portion folded over the inner portion, the inner portion and the folded portion defining a slot extending along the longitudinal axis of the seal anchor member; and
    a guide pin secured with the folded portion, the guide pin slidably engaging the slot defined in the inner portion to transition the first end to one of the plurality of states.

2. The surgical apparatus according to claim 1, wherein the plurality of states comprise a plurality of folded states.

3. The surgical apparatus according to claim 2, wherein the plurality of folded states include a maximum folded state corresponding to a minimum length of the seal anchor member.

4. The surgical apparatus according to claim 2, wherein the plurality of folded states include a minimum folded state corresponding to a maximum length of the seal anchor member.

5. The surgical apparatus according to claim 2, wherein the first end has an outer surface and an inner surface in each folded state.

6. The surgical apparatus according to claim 5, wherein the outer surface and the inner surface of the first end are connected.

7. The surgical apparatus according to claim 5, wherein the outer surface and the inner surface of the first end are sutured together.

8. The surgical apparatus according to claim 7, wherein the first end further defines an aperture configured to receive the guide pin disposed through the aperture and the slot to facilitate transition within the plurality of folded states.

9. The surgical apparatus according to claim 1, wherein the first end defines a first radial dimension, the second end defines a second radial dimension, and the first radial dimension is substantially larger than the second radial dimension.

10. The surgical apparatus according to claim 1, wherein the seal anchor member defines a substantial coring configuration therein creating an open space in a center region of the seal anchor member.

11. The surgical apparatus according to claim 1, wherein the seal anchor member exhibits an hourglass configuration elongated in a radial axis of the seal anchor member.

12. The surgical apparatus according to claim 11, further comprising a plurality of longitudinal ports.

13. The surgical apparatus according to claim 1, wherein the folded portion defines a bore configured to receive the guide pin therethrough.

14. The surgical apparatus according to claim 1, wherein at least a portion of the slot defined in the inner portion is in a superposed relation with the slot defined in the folded portion.

15. The surgical apparatus according to claim 1, wherein the slot defines a length along the longitudinal axis.

* * * * *